(12) United States Patent
Lisowsky et al.

(10) Patent No.: US 9,795,133 B2
(45) Date of Patent: Oct. 24, 2017

(54) SYNERGISTIC DISINFECTING COMPOSITIONS WITH ESSENTIAL OILS

(75) Inventors: Thomas Lisowsky, Monheim (DE); Karlheinz Esser, Moenchengladbach (DE)

(73) Assignee: MULTIBIND BIOTEC GMBH, Cologne (DE)

( * ) Notice: Subject to any disclaimer, the term of this patent is extended or adjusted under 35 U.S.C. 154(b) by 0 days.

(21) Appl. No.: 13/981,548

(22) PCT Filed: Jan. 24, 2012

(86) PCT No.: PCT/EP2012/051061
§ 371 (c)(1),
(2), (4) Date: Jul. 24, 2013

(87) PCT Pub. No.: WO2012/101129
PCT Pub. Date: Aug. 2, 2012

(65) Prior Publication Data
US 2013/0302434 A1   Nov. 14, 2013

(30) Foreign Application Priority Data
Jan. 26, 2011   (EP) .................... 11152241

(51) Int. Cl.
| | |
|---|---|
| *A61K 36/53* | (2006.01) |
| *A01N 37/04* | (2006.01) |
| *A01N 37/36* | (2006.01) |
| *A01N 65/00* | (2009.01) |
| *A01N 65/22* | (2009.01) |
| *A01N 65/28* | (2009.01) |
| *A01N 59/16* | (2006.01) |
| *A01N 63/02* | (2006.01) |

(52) U.S. Cl.
CPC ............ *A01N 37/04* (2013.01); *A01N 37/36* (2013.01); *A01N 59/16* (2013.01); *A01N 63/02* (2013.01); *A01N 65/00* (2013.01); *A01N 65/22* (2013.01); *A01N 65/28* (2013.01)

(58) Field of Classification Search
None
See application file for complete search history.

(56) References Cited

U.S. PATENT DOCUMENTS

| | | | |
|---|---|---|---|
| 6,294,186 B1* | 9/2001 | Beerse et al. ................. | 424/405 |
| 2007/0281857 A1 | 12/2007 | Wilson et al. | |
| 2008/0045491 A1* | 2/2008 | Fitchmun ..................... | 514/185 |
| 2009/0028961 A1 | 1/2009 | Lisowsky | |
| 2010/0119566 A1 | 5/2010 | Krug et al. | |
| 2010/0143431 A1 | 6/2010 | Landau et al. | |
| 2012/0107415 A1 | 5/2012 | Lisowsky et al. | |
| 2013/0158522 A1 | 6/2013 | Lisowsky et al. | |

FOREIGN PATENT DOCUMENTS

| | | |
|---|---|---|
| DE | 36 11 265 C2 | 1/1989 |
| DE | 10 2006 001213 A1 | 7/2007 |
| EP | 1 146 111 A1 | 10/2001 |
| EP | 1 167 510 A1 | 1/2002 |
| WO | 2007080108 A1 | 7/2007 |

\* cited by examiner

*Primary Examiner* — Terry A McKelvey
*Assistant Examiner* — Catheryne Chen
(74) *Attorney, Agent, or Firm* — Agris & Von Natzmer, LLP; Joyce Von Natzmer

(57) ABSTRACT

The present invention relates to new, highly efficient antimicrobial compositions comprising essential oils, metal ions, organic acids and detergents. Bacteria-containing samples treated with the complete synergistic disinfecting composition according to the invention (A or B or C or D+O) do not show any living cell colonies, indicating that under these conditions all microorganisms were killed. Thus it is proven that the synergistic mixtures of the compounds according to the invention show a very effective antimicrobial effect.

15 Claims, 2 Drawing Sheets a)

b)

SYNERGISTIC DISINFECTING COMPOSITIONS WITH ESSENTIAL OILS

CROSS-REFERENCE TO RELATED APPLICATIONS

This is the U.S. national stage of International application PCT/EP2012/051061, filed Jan. 24, 2012 designating the United States and claiming priority to EP 11152241.3, filed Jan. 26, 2011.

BACKGROUND

The present invention relates to new, highly efficient anti-microbial compositions comprising essential oils.

PRIOR ART

Microbial contaminations of surfaces cause severe problems and commercial losses, for example, in food processing and technology, in production facilities, in hospitals, diagnostic laboratories, public health, hygiene institutes, and also in the general household.

Therefore, already for a longer time many different decontamination and disinfection solutions exist that use aggressive chemical agents like for example formaldehyde, alcohols, phenols, sodium azide, sodium hypochloride or strong oxidizing agents like for example hypochloride, bleaching substances, peroxides or mineralic acids for killing all kind of microorganisms. Currently many commercial products contain such aggressive chemical solutions and are applied for spraying, washing and rinsing of equipment, instruments and surfaces. The major disadvantages of these solutions and methods are corrosive and irritating effects of the applied chemicals against equipment, instruments, surfaces and also against skin and mucous membranes of the user. Therefore biocompatible alternatives for disinfecting agents are getting more interest.

Essential oils are of special interest because they exhibit a broad spectrum of antiseptic activity. Tea Tree Oil (TTO) from *Melaleuca alternifolia* is one prominent example of essential oils with good biocidal action against bacteria and fungi. The publication of Carson et al. 2006 is a good review of the current knowledge about the antimicrobial properties of TTO (Carson, C. F., Hammer, K. A. and Riley, T. V. (2006). *Melaleuca alternifolia* (Tea Tree) Oil: a review of antimicrobial and other medicinal properties. Clinical Microbiology Reviews, Vol. 19, No. 1, 50-62).

In contrast to classical chemical biocides that are produced or synthesized in large amounts from industrial facilities the use of essential oils is dependent on and limited by the natural resources of the respective plants.

SUMMARY OF THE INVENTION

It is the object of the invention to overcome the current limitations and disadvantages of the prior art and to develop new compositions with higher antimicrobial efficiency.

The task to overcome the limitations and disadvantages of the prior art is accomplished by a disinfecting composition comprising a synergistic mixture of:
  a) at least one essential oil,
  b) at least one type of organic acid,
  c) at least one metal ion, and
  d) at least one surface-active compound.

Surprisingly, it was found that compositions comprising mixtures of essential oils, organic acids, detergents and metal ions exhibit significant higher antimicrobial activities than the substances alone or incomplete mixtures of them. Combining essential oils with organic acids, metal ions and surface-active agents enhances the antimicrobial activity of the essential oils and thereby allow formulations with lower essential oil concentrations that are still effective. Lower concentrations of active substances also have many other positive effects for biocompatibility, practical applications and commercial aspects.

Accordingly, the invention concerns a new synergistic disinfecting composition for the treatment of all kind of surfaces that are contaminated by unwanted microorganisms. For example, surfaces from rooms, walls, equipment, medical instruments, materials, but also skin, hand, body as well as the outer surfaces of plants, fruits and food are efficiently decontaminated. Microorganisms are killed with high efficiency by spraying, rubbing or immersion in solutions of the composition.

According to a preferred embodiment of the invention the etheric or essential oils are possibly but not exclusively selected from the following plant species as illustrating examples: tea tree (*Melaleuca alternifolia*) oil, lavender (*Lavandula angustifolia*) oil, pine (*Pinus silvestris*) oil, manuka (*Leptospermum scoparium*) oil, kanuca (*Kunzea ericoides*) oil, eucalyptus (*Eucalyptus globulus*) oil, bergamot (*Citrus bergamia*) oil, clove (*Eugenia caryaphylata*) oil, lemon (*Citrus limoneum*) oil, lemon grass (*Cymbpogon citratus*) oil, rosemary (*Rosmarinus officialis*) oil, geranium (*Pelargonium graveoleus*) oil, Nimtree (*Azadirachta indica*) oil, mint oil or any other composition containing menthol and/or menthene or any mixture thereof.

According to another preferred embodiment of the invention, the essential oil is included in the composition in concentrations from 0.01% to 10% (weight), preferably 0.01% to 5% (weight), more preferred 0.01% to 2% (weight), most preferred 0.01% to 1.0% (weight), in particular 0.02% to 1.0% (weight), in relation to the total weight of the composition. Accordingly, lower amounts of essential oil in the synergistic composition according to the invention are sufficient to achieve a significant antimicrobial effect.

The inventively applied metal ions are di- and/or trivalent ions of metals found in the 4th group and/or sub-group I, II and VIII of the periodic table of the elements. They may be used as salts in combination with their organic and/or inorganic acids and bases. According to the invention, it is preferred to select one or several compounds from sub-group VIII, especially iron, cobalt, nickel, copper or zinc.

The metal ions are preferably used in concentrations of 0.01 mM to 100 mM, preferably in concentrations of 0.01 mM to 10 mM, preferably 0.01 mM to 5 mM, more preferred 0.02 to 5 mM or 0.1 mM to 1.0 mM, most preferred 0.05 mM to 5 mM or 0.1 mM to 5 mM.

The organic acids that may be used in preparing the disinfecting composition of the present invention are either solid or liquid in their natural state and are readily soluble or dissolved in or miscible with water or an aqueous solvent. Exemplary organic acids include carboxylic acids such as citric acid, valeric acid, itaconic acid, acetic, citriconic acid, lactic acid, malic acid, succinic acid, aldaric acid, malonic acid, proprionic acid, malonic acid, maleic acid, salicylic acid, glutaric acid, tartaric acids, benzoic acid and the like. Preferably, the organic acid is included in the composition in concentrations from 0.1 mM to 500 mM, preferably 0.1 mM to 50 mM, more preferred 0.2 to 50 mM, most preferred 0.5 mM to 50 mM, in particular 1.0 mM to 50 mM or 1.0 mM to 10 mM.

The inventively applied surface-active substances may be anionic, non-ionic, amphoteric or cationic inert tensides or suitable mixtures thereof. Especially, alkylethersulfate, alkyl- and/or arylsulfonate, alkylsulfate, amphotensides, betaines, alkylamidoalkylamines, alkyl substituted amino acids, alkyl substituted imino acids, acylated amino acids, and amphotenside combinations can be used. In principle all inert tensides are suitable. Inert means, that they do not disturb or reduce the synergistic solution and its effects. Invention-related preferred are anionic and non-ionic tensides. Surface-active substances are preferably used in concentrations of 0.01% to 10% (weight), preferably 0.01% to 1% (weight), more preferred 0.01% to 0.5% (weight), most preferred 0.01% to 0.2% (weight), in particular 0.05 & to 0.15%, or about 0.1%, in relation to the total volume of the solution.

Preferred basic compositions and preferred mixtures of their components comprising essential oils, organic acids, detergents (surface-active substances) and metal ions for the disinfecting composition according to the invention are:

Essential oils: 0.01%-10%, most preferred 0.02%-1%
Organic acids: 0.1 mM-100 mM, most preferred 1.0 mM-50 mM
Detergents: 0.01%-10%, most preferred about 0.1%
Metal ions: 0.01 mM-50 mM, most preferred 0.1 mM-5 mM Preferably, the ratio of organic acids and metal ions is adjusted to about 10:1 (organic acid:metal ions [M]).

The invention-related disinfecting composition may comprise additional common inert adjuvants and additives like, for example, suitable buffer substances for defining a specific pH value, like Tris (Tris(hydroxymethyl)-aminomethan), MES (2(Morpholino)ethansulfonic acid), HEPES (2-[4-(2-Hydroxyethyl)-1-piperazinyl]-ethansulfonic acid, MOPS (3-(N-Morpholino)propansulfonic acid), carbonate and derivates of succinic acid. The buffer systems are preferably used in concentrations of 1 mM to 500 mM in relation to the total volume of the solution.

For better solubility of the essential oils and also for better wetting of surfaces all kind of alcohols can be added like, for example, ethanol, isopropanol or others. Bioethanol is an especially preferred additive for this purpose, because it supports the biocompatibility of the composition. In principle, all additives that adjust the physical properties of the composition for specific applications may be added to the composition according to the invention.

Advantageously, the disinfecting composition according to the invention has a pH value in the range between pH 2 and 6 so that effective killing of microorganisms is guaranteed. This is an important aspect of the invention since, surprisingly, it turned out that the disinfecting effect of essential oils is significantly reduced in basic solutions. Also the here described new synergistic effect is significantly reduced at pH values higher than pH 6. It is therefore an advantage of the compositions according to the invention that they inherently have an acidic pH value. If necessary, the pH value of the composition according to the invention can be optionally adjusted to a pH between 2 and 6 by varying the concentration of the organic acid or by adding substances suitable for pH adjustment.

Thereby all kind of surfaces can be treated in a very gentle, biocompatible way for killing and removal of microorganisms.

The disinfecting composition according to the invention can be used for treating contaminated surfaces, preferably surfaces of medical instruments, plants or food.

Accordingly, the invention concerns a method for disinfecting a contaminated surface, comprising the following step:

applying a composition to the surface, wherein said composition comprises at least one essential oil, at least one type of organic acid, at least one metal ion, and at least one surface-active compound.

In general, decontamination is achieved by spraying or rubbing the composition according to the invention onto contaminated surfaces or by immersion. A residence time of 0.5 to 5 minutes at room temperature or slightly higher temperatures is normally sufficient for complete elimination of living microorganisms from surfaces.

The applied methods are however variable and can be adjusted to the different tasks.

In the following, the invention is exemplarily illustrated in detail with reference to the figures and tables.

Each aliquot contains $10^4$ cells of *Candida parapsilosis*. The growth plates are incubated at 28° C. for 48 h.
Tested Solutions:
Tea tree oil (TTO) in concentrations of 1% to 0.02%, 0=control without any TTO;
Mixtures of organic acids, metal ions and detergent include citrate: $FeCl_3$ in molar ratios of 10:1 and detergent, which is always SDS, in a concentration of 0.1%;
The pH range of the solutions is from pH 2.0 to pH 4.0 in relation to the concentration of citrate;
Control (0/0): without any substances.

DESCRIPTION OF EXEMPLARY AND PREFERRED EMBODIMENTS

Figure 1:
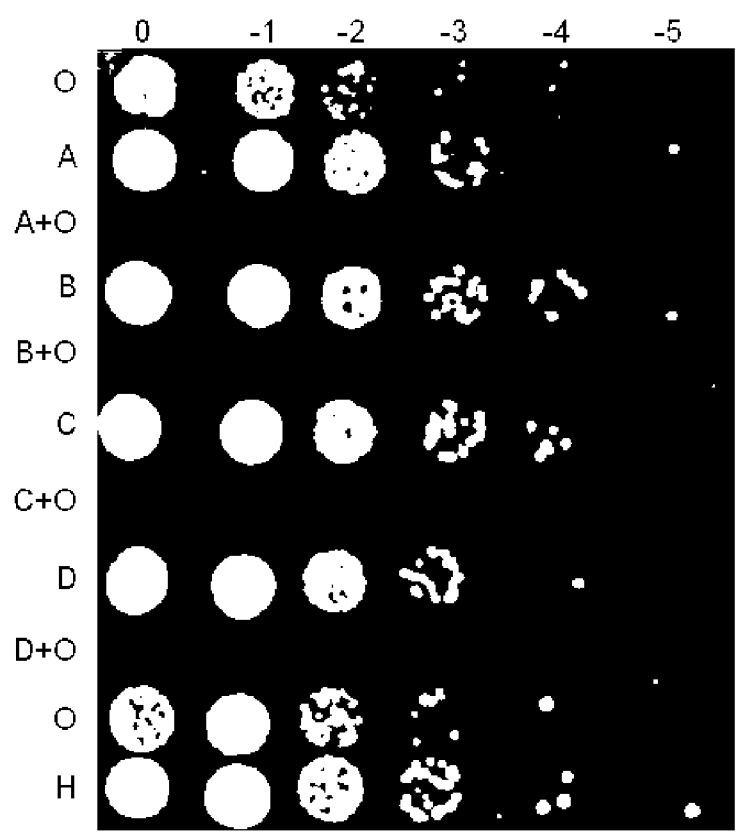
FIG. 1 shows the synergistic effect of a composition according to a preferred embodiment of the invention on bacterial suspension cultures of *Escherichia coli* (DSM 498). Labeling of the figure is:
O: organic acid mixture
A: 0.5% eucalyptus oil
A+O: 0.5% eucalyptus oil+organic acid mixture
B: 0.5% rosemary oil
B+O: 0.5% rosemary oil+organic acid mixture
C: 0.5% melissa oil
C+O: 0.5% melissa oil+organic acid mixture
D: 0.5% tea tree oil
D+O: 0.5% tea tree oil+organic acid mixture
O: organic acid mixture
H: control with sterile $H_2O$
Composition of the organic acid mixtures (O):
1 mM citrate, 100 µM $FeCl_3$, 0.01% SDS in sterile water

FIG. 1 shows the beneficial effect of a composition according to a preferred embodiment of the invention on bacterial suspension cultures. Test solutions are: a) sterile water (H), b) essential oils (A, B, C, D), c) organic acid mixtures (O) or d) the synergistic compositions with essential oils and organic acid mixtures (A or B or C or D+O). After an incubation time of 30 sec. (*Escherichia coli*), the 100 µl samples containing the microorganisms were neutralized and 10 µl aliquots were plated in dilutions of 0, $10^{-1}$, $10^{-2}$, $10^{-3}$, $10^{-4}$, $10^{-5}$ onto growth media. After an incubation period of 1 day at 37° C., a digital image of the growth plate was taken. In test samples with sterile water (H) or the mixture containing organic acid (O) all microorganisms survived. Samples treated with the complete synergistic disinfecting composition according to the invention (A or B or C or D+O) did not show any living cell colonies, indicating that under these conditions all microorganisms were killed. Thus it is proven that the different substances alone do not exhibit a special antimicrobial effect and also the mixtures of the components outside the scope of the invention are not effective or do only show a limited effect. Surprisingly, the synergistic mixtures of the compounds according to the invention show a very effective antimicrobial effect.

Figure 2:
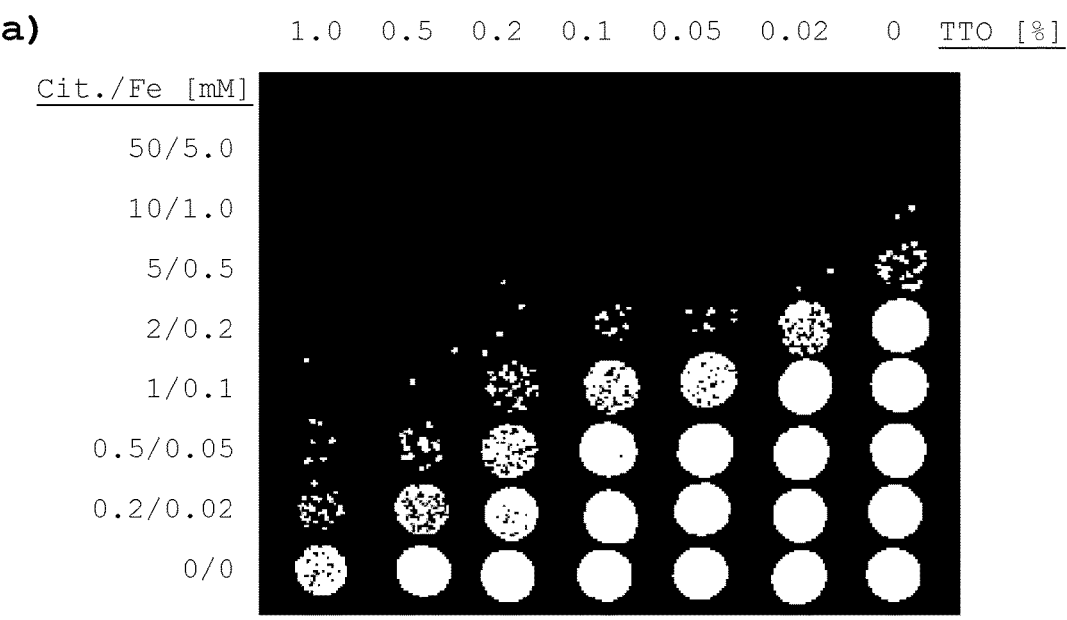
FIG. 2 shows the effect of different compositions according to preferred embodiments of the invention on suspension cultures of *Candida parapsilosis*. The microorganisms are incubated in respective synergistic mixtures at room temperature (RT) with residence times of
a) 5 minutes and
b) 30 minutes.
Figure 2:
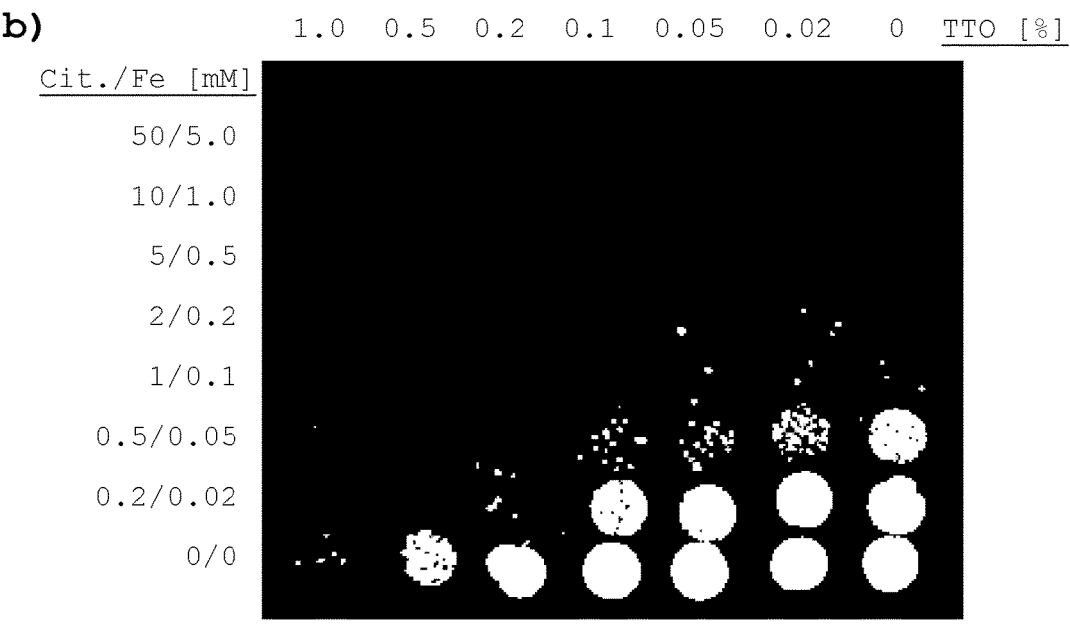

FIG. 2 shows the beneficial effect of different compositions according to preferred embodiments of the invention on suspension cultures of *Candida parapsilosis*. The microorganisms are incubated in respective synergistic mixtures at room temperature (RT) with residence times of 5 and 30 minutes, respectively. After neutralizing mixtures and dilutions, identical aliquots are tested for surviving cells.

A digital image of the growth plate was taken after incubation. Spots showing no or only few *Candida* colonies represent compositions having optimal or at least sufficient anti-microbial properties. It is observed that the disinfecting effect of the compositions according to the invention increases with increasing concentrations of their components and that concentration of the essential oil can be reduced with increasing concentrations of organic acid and metal ions. As becomes apparent from FIG. 2, the general efficiency of antimicrobial action of essential oil is enhanced by the other components of the synergistic mixtures, i.e. lower concentrations of essential oil and shorter residence times are effective only with synergistic mixtures. Accordingly, there is a synergistic effect in relation to residence time and essential oil concentration, especially in the range between 50:5 and 1:0.1 organic acids:metal ions with 0.1% detergent. The pH range of the solutions is from pH 2.0 to pH 4.0 in relation to the concentration of citrate. With synergistic mixtures the amount of essential oils, which have an undesired toxic effect in higher concentrations, can be substantially and advantageously reduced in all formulations.

Table 1 summarizes tests with bacterial suspension cultures of *Escherichia coli* (DSM 498) for the anti-bacterial efficiency of the new synergistic compositions in comparison to controls.

Table 2 summarizes tests with yeast suspension cultures of *Candida parapsilosis* (DSM 70125) for the anti-fungal efficiency of the new synergistic compositions in comparison to controls.

In all experiments freshly grown cultures of the listed microorganisms were adjusted to a cell number of $10^7$ in a 100 µl volume of the test solutions. Test solutions are: a) sterile water, b) essential oils c) organic acid mixtures or d) a synergistic disinfecting composition according to the invention including essential oils, organic acid, metal ions and detergent. After an incubation time of 30 sec. (*Escherichia coli*) or 1 hour (*Candia parapsilosis*) the 100 µl samples containing the microorganisms were neutralized and 10 µl aliquots were plated in dilutions of 0, $10^{-1}$, $10^{-2}$, $10^{-3}$, $10^{-4}$, $10^{-5}$ onto growth media. After an incubation period of 1-3 days at 28° C. (*Candida parapsilosis*) or 37° C. (*Escherichia coli*) the number of grown colonies was determined. In test samples with sterile water or the mixture containing organic acid all microorganisms survived. Samples treated with the complete synergistic disinfecting composition according to the invention did not show any living cell colonies, indicating that under these conditions all microorganisms were killed. Four essential oils represented by tea tree oil, eucalyptus oil, rosemary oil and melissa oil were tested and gave comparable results for efficient killing of the microorganisms in synergistic compositions.

TABLE 1

Summary of tests with bacterial suspension cultures of *Escherichia coli* (DSM 498) for anti-bacterial efficiency of the new synergistic compositions in comparison to controls.

| | a) $H_2O$ | B) essential oils alone | c) organic acid mixtures alone | d) synergistic compositions |
|---|---|---|---|---|
| survival of bacteria after 30 sec. | $10^5$ | $10^5$ | $10^5$ | 0 | a) $H_2O$: control with only sterile water
b) Essential oil: control with essential oils alone:
0.5% tea tree oil in sterile water
0.5% eucalyptus oil in sterile water
0.5% rosemary oil in sterile water
% melissa oil in sterile water
c) Organic acid mixtures alone:
1 mM citrate, 100 µM $FeCl_3$, 0.01% SDS in sterile water
d) Tested synergistic compositions:
0.5% tea tree oil, 1 mM citrate, 100 µM $FeCl_3$, 0.01% SDS in sterile water,
0.5% eucalyptus oil, 1 mM citrate, 100 µM $FeCl_3$, 0.01% SDS in sterile water,
0.5% rosemary oil, 1 mM citrate, 100 µM $FeCl_3$, 0.01% SDS in sterile water, and
0.5% melissa oil, 1 mM citrate, 100 µM $FeCl_3$, 0.01% SDS in sterile water.
Incubation time of bacteria with solutions for all tests: 30 seconds.

TABLE 2

Summary of tests with yeast suspension cultures of *Candida parapsilosis* (DSM 70125) for anti-fungal efficiency of the new synergistic compositions in comparison to controls.

| | a) $H_2O$ | b) essential oils alone | c) organic acid mixtures alone | d) synergistic compositions |
|---|---|---|---|---|
| survival of yeast cells after 60 min. | $10^5$ | $10^5$ | $10^5$ | 0 | a) $H_2O$: control with only sterile water
b) Essential oil: control with essential oils alone:
1% tea tree oil in sterile water
1% eucalyptus oil in sterile water
1% rosemary oil in sterile water
1% melissa oil in sterile water
c) Organic acid mixtures alone:
2 mM citrate, 200 µM $FeCl_3$, 0.02% SDS in sterile water
d) Tested synergistic compositions:
1% tea tree oil, 2 mM citrate, 200 µM $FeCl_3$, 0.02% SDS in sterile water,
1% eucalyptus oil, 2 mM citrate, 200 µM $FeCl_3$, 0.02% SDS in sterile water,
1% rosemary oil, 2 mM citrate, 200 µM $FeCl_3$, 0.02% SDS in sterile water, and
1% melissa oil, 2 mM citrate, 200 µM $FeCl_3$, 0.02% SDS in sterile water.
Incubation time for yeast cells with solutions in all tests: 60 minutes.

LITERATURE

Carson, C. F., Hammer, K. A. and Riley, T. V. (2006). *Melaleuca alternifolia* (Tea Tree) Oil: a review of antimicrobial and other medicinal properties. Clinical Microbiology Reviews, Vol. 19, No. 1, 50-62.

The invention claimed is:
1. A disinfecting composition comprising a synergistic mixture of:

a) at least one essential oil in concentrations from 0.02% to 1% (weight) in relation to the total weight of the composition,
b) at least one type of organic acid in concentrations from 1 mM to 50 mM,
c) at least one metal ion in concentrations from 0.1 mM to 5 mM, and
d) at least one surface-active compound in concentrations from 0.01% to 0.5% (weight) in relation to the total weight of the composition,
   wherein the molar ratio of the organic acid and the metal ion is adjusted to about 10:1.

2. The disinfecting composition according to claim 1 wherein the metal ion is selected from the $4^{th}$ group or sub-groups I, II, or VIII of the periodic table of the elements.

3. The disinfecting composition according to claim 1, wherein the metal ion is a salt of a respective acid or base.

4. The disinfecting composition according to claim 1, wherein the surface-active substance is at least one compound selected from the group consisting of anionic, nonionic, amphoteric or cationic tensides and mixtures thereof.

5. The disinfecting composition according to claim 1, wherein the surface-active compound is included in concentrations from 0.01% to 0.2 (weight) in relation to the total weight of the composition.

6. The disinfecting composition according to claim 1, further comprising additives including buffer substances or alcohols.

7. The disinfecting composition according to claim 1, wherein a pH value of the composition is in the range between pH 2 and 6.

8. A method for disinfecting a contaminated surface, said method comprising:
   applying a composition to the surface, wherein said composition comprises the composition of claim 1, and
   disinfecting the contaminated surface as a result of this applying.

9. The method of claim 8, wherein the contaminated surface is a surface of a medical instrument, a plant or food.

10. The disinfecting composition according to claim 1, wherein the metal ion is included in concentrations from 0.1 mM to 1.0 mM.

11. The disinfecting composition according to claim 5, wherein the surface-active compound is included in concentrations from 0.05% (weight) to 0.15% (weight) in relation to the total volume of the composition.

12. The disinfecting composition of claim 1, wherein said at least one type of organic acid is a carboxylic acid or/and the at least one metal ion is a group VIII metal ion.

13. The disinfecting composition of claim 12, wherein said at least one type of organic acid is a carboxylic acid and the at least one metal ion is a group VIII metal ion.

14. The disinfecting composition of claim 4, wherein said at least one type of organic acid is a carboxylic acid or/and the at least one metal ion is a group VIII metal ion.

15. The disinfecting composition of claim 14, wherein said at least one type of organic acid is a carboxylic acid and the at least one metal ion is a group VIII metal ion.

* * * * *